(12) United States Patent
Duong et al.

(10) Patent No.: US 8,426,806 B2
(45) Date of Patent: Apr. 23, 2013

(54) DIFFERENTIAL MOBILITY SPECTROMETER WITH SPATIAL ION DETECTOR AND METHODS RELATED THERETO

(75) Inventors: Tuan A. Duong, Glendora, CA (US); Isik Kanik, Monrovia, CA (US); Vu A. Duong, Rosemead, CA (US)

(73) Assignee: California Institute of Technology, Pasadena, CA (US)

( * ) Notice: Subject to any disclaimer, the term of this patent is extended or adjusted under 35 U.S.C. 154(b) by 63 days.

(21) Appl. No.: 12/973,843

(22) Filed: Dec. 20, 2010

(65) Prior Publication Data

US 2012/0132795 A1    May 31, 2012

Related U.S. Application Data

(60) Provisional application No. 61/288,755, filed on Dec. 21, 2009.

(51) Int. Cl.
*B01D 59/44* (2006.01)
(52) U.S. Cl.
USPC .......................................... 250/282; 250/281
(58) Field of Classification Search .................. 250/281, 250/282, 286, 290, 293, 299, 300
See application file for complete search history.

(56) References Cited

U.S. PATENT DOCUMENTS

| | | | | |
|---|---|---|---|---|
| 6,521,887 B1* | 2/2003 | Funsten et al. | ................ | 250/287 |
| 7,388,196 B1* | 6/2008 | Hagerman | ................... | 250/291 |
| 7,408,152 B2* | 8/2008 | Holle et al. | .................... | 250/288 |
| 7,735,146 B2* | 6/2010 | Vertes et al. | ..................... | 850/9 |
| 7,807,963 B1* | 10/2010 | Bier | .............. | 250/283 |
| 2003/0071223 A1* | 4/2003 | Hartley et al. | ............. | 250/423 F |
| 2007/0252082 A1* | 11/2007 | Miller et al. | ................. | 250/282 |
| 2009/0179147 A1* | 7/2009 | Milgram et al. | ............. | 250/282 |
| 2009/0261243 A1* | 10/2009 | Bamberger et al. | .......... | 250/287 |
| 2010/0123075 A1* | 5/2010 | Dantus et al. | ................. | 250/282 |
| 2010/0294924 A1* | 11/2010 | Brouard et al. | .............. | 250/282 |
| 2011/0139973 A1* | 6/2011 | Bowdler | .................... | 250/252.1 |
| 2012/0025068 A1* | 2/2012 | Clench et al. | ................. | 250/282 |

OTHER PUBLICATIONS

Fuerstenau, S., et al. Active pixel sensors for mass spectrometry, International Journal of Mass Spectrometry 2002, 215: 101-111.
Duong, T.A., et al., Convergence analysis of cascade error projection-an efficient learning algorithm for hardware implementation, International Journal of Neural Systems, 2000, vol. 10, No. 3, pp. 199-210.
Shvartsburg, A.A., et al., Feasibility of Higher-Order Differential Ion Mobility Separations Using New Asymmetric Waveforms, J. Phys. Chem. A, 2006, vol. 110, pp. 2663-2673.

* cited by examiner

*Primary Examiner* — Robert Kim
*Assistant Examiner* — Jason McCormack
(74) *Attorney, Agent, or Firm* — Steinfl & Bruno LLP

(57) ABSTRACT

Differential mobility spectrometer with spatial ion detector and methods related thereto are disclosed. The use of one or more spatial detector within differential mobility spectrometry can provide for the identification and separation of ions with similar mobility and mass.

17 Claims, 6 Drawing Sheets

$$h = \frac{KEL}{V_d}$$

DIFFERENTIAL MOBILITY SPECTROMETER WITH SPATIAL ION DETECTOR AND METHODS RELATED THERETO

CROSS REFERENCE TO RELATED APPLICATIONS

The present application claims priority to U.S. Provisional Application No. 61/288,755, filed on Dec. 21, 2009, which is incorporated herein by reference in its entirety.

STATEMENT OF GOVERNMENT GRANT

The invention described herein was made in the performance of work under a NASA contract, and is subject to the provisions of Public Law 96-517 (35 USC 202) in which the Contractor has elected to retain title.

FIELD

The present disclosure relates to ion mobility spectrometry. In particular, it relates to a differential mobility spectrometer with spatial ion detector and methods related thereto.

BACKGROUND

Detection of chemical compounds can be performed by ionizing substances in air at ambient pressure and characterizing ions contained in the substances. Performing this characterization in air at ambient pressure allows for use of inexpensive and robust analyzers. Such detection methods are used today in, for instance, ion mobility spectrometry (IMS) and differential mobility spectrometry (DMS).

In the traditional method of drift-time IMS, commonly referred to as just IMS, ions obtained from a substance travel through a drift chamber, which has an applied electric field that affects ion trajectory and a carrier buffer gas that opposes ion motion. At the end of the drift chamber is a detector. An ion's mobility is a function of its mass, charge, size, and shape. As a result of different ion mobility of different ions, migration time through the drift chamber of each type of ion is different, leading to the ability to distinguish different ion species.

SUMMARY

According to a first aspect, a system for detecting and identifying ions is provided, the system comprising: an entry portion for ions; a chamber through which the ions traverse during operation; an electric field generator coupled to the chamber, wherein pulses of electric field generated by the electric field generator are adapted to direct the ions in the chamber; a spatial detector configured to receive a first set of ions, the spatial detector comprising a first plurality of detector pixels arranged in a two-dimensional array, wherein each detector pixel in the first plurality of detector pixels is associated with an address and is configured to receive at least one ion in the first set of ions and to convert the at least one ion into a first voltage signal; a readout module adapted to select detector pixels from among the first plurality of detector pixels and read the first voltage signals and the addresses of the selected detector pixels, thus detecting the at least one ion; and a chemical recognition module configured to receive the first voltage signals and the addresses from the readout module and identify at least one ion in the first set of ions based on the first voltage signals and the addresses.

According to a second aspect, a system for detecting and identifying a target ion is provided, the system comprising: an entry portion for ions, wherein the ions comprise the target ion; a chamber through which the ions are adapted to traverse; an electric field generator coupled to the chamber, wherein a first set of pulses of electric field generated by the electric field generator are adapted to direct the ions in the chamber; a spatial detector configured to receive a first set of ions, the spatial detector comprising a first plurality of detector pixels arranged in a two-dimensional array, wherein each detector pixel in the first plurality of detector pixels is associated with an address and is configured to receive at least one ion in the first set of ions and convert the at least one ion into a first voltage signal; a separating detector configured to receive a second set of ions, the separating detector comprising a second plurality of detector pixels arranged in a two-dimensional array, wherein each detector pixel in the second plurality of detector pixels is associated with an address and is configured to receive at least one ion in the second set of ions, the second set of ions being a full set or subset of ions in the first set of ions, and is configured to convert the at least one ion into a second voltage signal; a readout module adapted to select detector pixels from among the first and second plurality of detector pixels and read the first and second voltage signals of the selected detector pixels, thus detecting the target ion; a chemical recognition module configured to: receive the first and second voltage signals and the addresses from the readout module identify at least one ion in each of the first and second set of ions based on the first and second voltage signals and addresses of the selected detector pixels; calculate data for a second set of pulses of electric field to direct the second set of ions to the separating detector; and iteratively receive, identify and calculate until the target ion is detected and identified at the separating detector, wherein the first set of ions initially comprises the target ion; and an electric field controller configured to receive the data for the second set of pulses of electric field from the chemical recognition module and to adjust the pulses of electric field applied to the chamber by the electric field generator based on the data.

According to a third aspect, a method for detecting and identifying ions is provided, the method comprising: a) providing ions to an entry portion of a chamber; b) directing the ions through the chamber by applying a first set of pulses of electric field to the chamber; c) receiving a first set of ions at a spatial detector, the spatial detector comprising a first plurality of detector pixels arranged in a two-dimensional array, wherein each detector pixel is associated with an address and receives none, a subset, or a full set of the ions in the first set of ions; d) converting the first set of ions to a set of first voltage signals; e) selecting detector pixels from among the first plurality of detector pixels; f) reading the first voltage signal and the address of each selected detector pixel, thus detecting ions; and g) identifying ions received at each selected detector pixel based on the first voltage signal and the address of each selected detector pixel.

According to a fourth aspect, a method for detecting and identifying a target ion is provided, the method comprising: a) providing ions to an entry portion of a chamber, wherein the ions comprise the target ion; b) directing the ions in the chamber by applying a first set of pulses of electric field to the chamber; c) receiving a first set of ions at a spatial detector, the spatial detector comprising a first plurality of detector pixels arranged in a two-dimensional array, wherein each detector pixel is associated with an address; d) converting the first set of ions to a set of first voltage signals; e) selecting at least one detector pixel from among the plurality of detector pixels; f) reading the first voltage signal and the address of each selected detector pixel, thus detecting ions; and g) identifying ions received at each selected detector pixel based on the first voltage signal and the address of each selected detector pixel.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 3B also shows the exemplary 2-D spatial detector generating voltage signals from the received ions.

APPENDICES

Figure 1A:
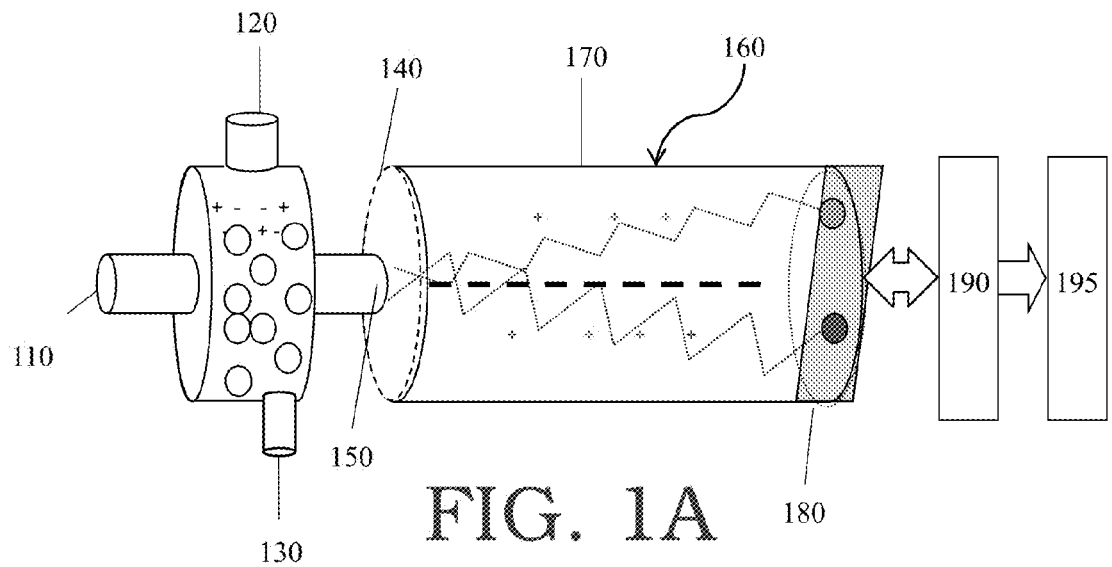
FIG. 1A shows an exemplary system for detection and identification of ions that uses a cylindrical chamber.

Appendix 1 and Appendix 2 are enclosed herewith and form integral parts of the specification of the present application.

DETAILED DESCRIPTION

In what follows, differential mobility spectrometer with spatial ion detector and methods related thereto are described in accordance with various embodiments of the present disclosure.

For clarity purposes, the term "ion" is defined herein as any type of atom or molecule containing one or more positive or negative charges. For example, a particular ion can be one or more atoms of the $Na^+$ ion. The particular ion can also be one or more molecules of the $OH^-$ ion. Additionally, the term "mass" is defined herein as atomic mass or molecular mass of the ion, with units of atomic mass unit (amu).

Differential mobility spectrometry (DMS), as a specific type of ion mobility spectrometry (IMS), is amenable to micro-fabricated drift chambers, comparatively simple electronics, low cost, and rugged configuration and allows for a real time, light weight, and pump free system. In particular, DMS can be used in a variety of portable applications where cost, size, energy consumption, and ruggedness are relevant factors while maintaining good performance. These characteristics make DMS of interest in space missions, for instance, where DMS may be used to detect and identify chemical compounds such as amino acids in life detection missions.

In general, DMS technology utilizes dependence of ion mobility on electric field strength E at high electric fields to separate ions. In particular, when the electric field strength is sufficiently high (e.g., greater than around 3000 V/cm), ion mobility K depends on the electric field strength as shown below:

$$K(E)=K_o(0)(1+f(E)),$$

where $f(E)$ is a positive function of E and $K_o(0)$ is the ion mobility constant at zero electric field and under standard conditions (e.g., pressure=760 Torr, temperature=273 K). Functionally, $K_o(0)$ is typically approximated by measuring ion mobility at low electric field.

An exemplary reference directed to the dependence of the ion mobility on electric field strength is Shvartzburg et al., 2006 *J. Phys. Chem.* 110 2663-2673, which is incorporated herein by reference in its entirety.

DMS technologies generally utilize the time domain to separate ions. However, standard use of the time domain to separate ions means that a DMS system that employs a detector with a slow time response, such as a big faraday plate detector, would be incapable of differentiating between ions in a chemical sample with nearly identical ion mobility and mass.

For example, an ion with a mass of 200 amu and another ion with a mass of 201 amu can arrive at the detector with insufficient time separation and can result in ambiguous chemical identification. Also, the use of the time domain for separation can result in slow acquisition time as the DMS system must scan through a range of ion mobilities to find ions of interest.

Instead of using time domain separation, the Applicants disclose a DMS system that utilizes two-dimensional spatial detector arrays (also referred to simply as a 2-D spatial detector) and functions in a high electric field. In this DMS system, electric field dependence of ion mobility is used to create spatial separation between different ions. Different ions refer to ions that have different ion mobilities and/or masses. The high electric field would be generated so as to yield sufficiently large separation in trajectories of the ions such that the ions hit the 2-D spatial detector at distinct detector pixels of the 2-D spatial detector.

Detection and identification of ions by the 2-D spatial detector allows for faster detection and identification of the ions and can be more sensitive than separation utilizing time duration alone at a single detector. In addition, use of an intelligent readout and a neural network process can further increase speed and accuracy of ion identification. Also, the 2-D spatial detector can be designed to collect data with spatial symmetry with respect to the drift chamber, thus inducing a separation of noise data from data of interest. Some or all of the above features can be incorporated in the various embodiments of the present disclosure for robust detection and identification of ions with similar mass and/or ion mobility.

In the present disclosure, a high electric field is employed to control the trajectory of the ions, where one or more 2-D spatial detectors are used to collect the ions. Detection and identification of each ion can be performed based on a voltage signal and an address read from each detector pixel in the one or more 2-D spatial detectors.

Figure 6:
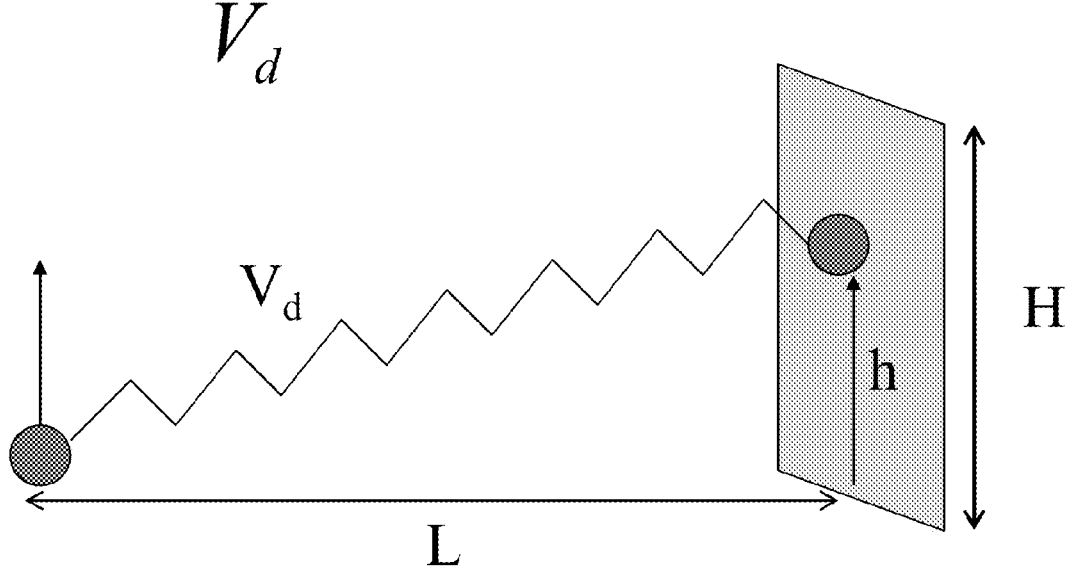
FIG. 6 shows an exemplary trajectory of an ion.

When ions are in presence of an electric field E, trajectory of any particular ion can be illustrated as shown in FIG. 6. As shown in FIG. 6, from its initial position, an ion will traverse a horizontal distance L and a vertical distance h, where the vertical distance is induced by the applied electric field E. The relationship between the distances and the electric field is given by $h=KEL/V_d$, where K is ion mobility and $V_d$ is drift velocity. As previously mentioned, at high electric fields, the ion mobility of an ion becomes a noticeable function of electric field.

Figure 2A:
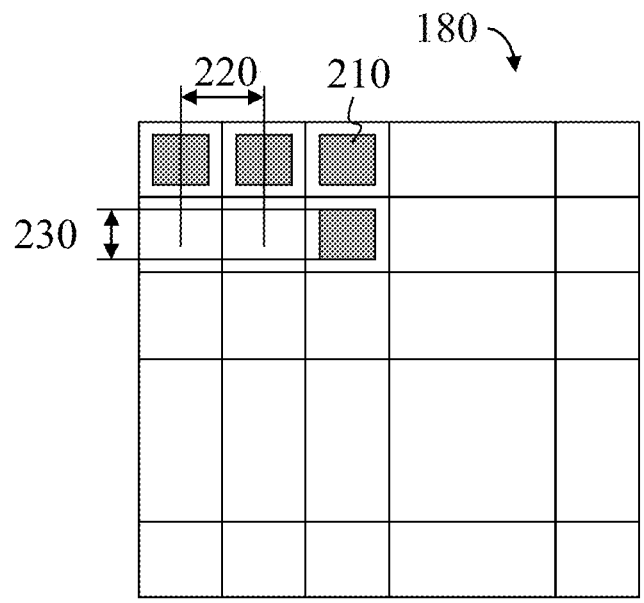
FIG. 2A shows an exemplary 2-D spatial detector.
Figure 2B:
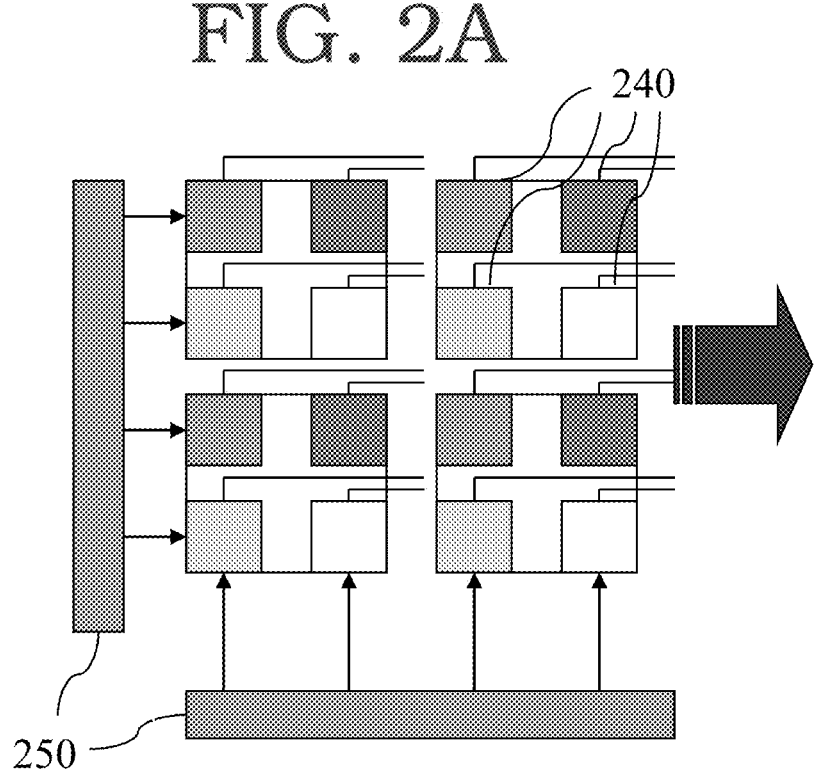
FIG. 2B shows an exemplary 2-D spatial detector configured for parallel readout.

Due to different trajectories for the different ions resulting from the applied electric field, the spatial separation of ions can be sufficient to land in different pixels of a 2-D spatial detector based on electric field controlled ion trajectories. For ions of very close ion mobilities and/or molecular mass, a high electric field is generally employed to obtain sufficient separation. FIGS. 2A and 2B show exemplary 2-D spatial detectors.

FIG. 1A shows an exemplary system according to the present disclosure that can be utilized as a differential mobility spectrometer for detection and identification of ions. The system comprises a sample inlet (110), an ionization source (120), a gas outlet (130), an ion entry portion (150), an ion entry controller (140), a chamber (160), an electric field generator (170), a spatial detector (180), a readout module (190), and a chemical recognition module (195).

The sample inlet (110) introduces a vaporized chemical sample. The ionization source (120) ionizes the vaporized chemical sample using ionization source gasses to produce ions for detection and identification. The gas outlet (130) removes excess vaporized chemical sample and ionization source gases.

Figure 1B:
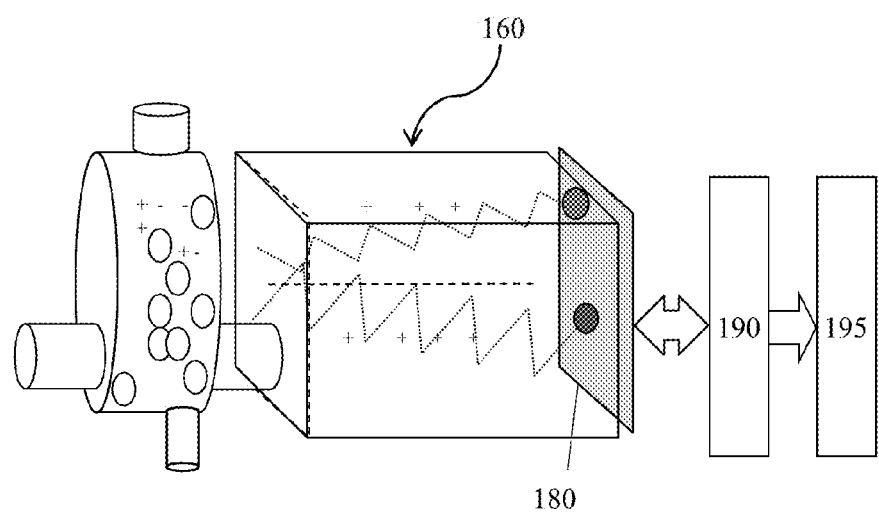
FIG. 1B shows an exemplary system for detection and identification of ions that uses a rectangular chamber.

The chamber (160), also referred to as drift chamber or drift tube, can be a circular or rectangular tube through which the ions traverse during operation. FIG. 1B shows an exemplary system that comprises a rectangular chamber (160). The chamber (160) can comprise the ion entry portion (150) through which the ions can enter the chamber (160). Entry of ions into the chamber (160) through the ion entry portion (150) can be controlled by the ion entry controller (140), which can be, for instance, an ion shutter.

The spatial detector (180) can be the aforementioned 2-D spatial detector array that comprises a 2-D array of detector pixels, such as the detector shown in FIGS. 2A and 2B. Each detector pixel of the spatial detector (180) can be associated with an address, (used to identify its location in the spatial detector (180)), receives ions, and converts the received ions into a voltage signal adapted to be read by the readout module (190).

The spatial detector (180) can be located in the chamber (160) at an opposite end of the chamber (160) from the ion entry portion (150), as shown in FIG. 1A. A person skilled in the art will understand that, while the drawing shows the spatial detector (180) at the end of the chamber, the spatial detector (180) can be in the chamber (160) or adjacent to the end (i.e., slightly outside) of the chamber (160). When outside of the chamber (160), distance of the spatial detector (180) from the end of the chamber (160) involves consideration of air flow within an air gap between the spatial detector (180) and the end of the chamber (160) and the applied electric field.

The readout module (190) can be an "intelligent" system such as one that selects groups of detector pixels and reads each selected group of detector pixels in parallel. Reading groups of multiple detector pixels in parallel generally yields faster data acquisition relative to reading each detector pixel individually. Mapping of an N×N group to a linear group of $N^2$ switches can be done by using matrices of transistor switches, wherein each element in the matrix corresponds with a particular transistor switch, as discussed in Appendix 1, and can result in fast, parallel processing of data from the detector pixels for recognition of patterns, such as the presently disclosed identification of ions. Appendix 1, which forms an integral part of the present disclosure, is herein incorporated in its entirety.

In another embodiment of the present disclosure, the readout module (190) can select only the detector pixels expected to be associated with a target ion to be read. Reading fewer detector pixels or fewer groups of detector pixels are examples of methods that can allow for faster operation of the ion detection and identification system.

The chamber (160) shown in FIGS. 1A and 1B can also be coupled to the electric field generator (170). The electric field generator (170) can be, for example, a system comprising a battery or a power supply and switches to generate pulses of the electric field.

The electric field generator (170) generates sets of pulses of electric field that are applied to the chamber (160), where the pulses are adapted to direct the ions from the ion entry portion (150) through the chamber (160) to the spatial detector (180). The pulses of electric field are also configured to separate the ions such that different types of ions will land in different detector pixels of the spatial detector (180).

The pulses of electric field used by the system can be square waves as described by Shvartzburg et al. in [Shvartzburg et al. 2006 *J. Phys. Chem.* 110 2663-2672]. However, for instance, Shvartzburg et al. requires integration of the applied electric field to be zero so that the ion mobility can be calculated explicitly. Such a limitation does not apply for the 2-D spatial detector system disclosed in the present disclosure since determination of the ion mobility is not always required, as later discussed in the present application. Specifically, the pulses of electric field of the present disclosure can also be sinusoidal waves, triangular waves, and so forth.

The system shown in FIGS. 1A and 1B can further comprise a chemical recognition module (195), which can receive the voltage signals of the selected detector pixels from the readout module (190) and identify the ions received by the spatial detector (180) based on the voltage signals and the addresses (locations) of the selected detector pixels. The chemical recognition module (195) can be a processor with a lookup table of voltage signals and detector pixel addresses for known types of ions that is used to identify the ions received by each of the selected detector pixels.

The chemical recognition module (195) can also contain a neural network unit, which can be implemented as hardware, software, or both, used for identifying ions through learning spatial and temporal patterns for ions impinging on the detectors as well as patterns in environmental variables such as temperature, pressure, and noise. The neural network unit may be used in conjunction with the lookup table, where values in the lookup table may be adjusted in response to information learned and derived by the neural network unit. The neural network unit can also be implemented to calculate feature-based descriptors to predict the ion mobility, which can then be used to calculate expected detector pixel (210) (location) where each target ion will hit the spatial detector (180). This implementation is discussed in Appendix 2, which forms an integral part of the present disclosure, and is herein incorporated in its entirety.

The chemical recognition module (195) can also operate according to a cascade error projection method to use hardware learning for the possible mapping of target ions to associated detector pixels. The use of cascade error projection method for efficient learning is discussed in [Duong and Stubberud, 2000, *Int. J. Neural Sys.* 10 199-210], the contents of which are also incorporated herein in its entirety by reference.

FIG. 2A shows that the spatial detector (180) of FIGS. 1A and 1B can comprise a plurality of detector pixels (210), arranged in a two-dimensional array. Each detector pixel (210) can have a pixel size (230) along the length of the detector pixel (210). The detector pixels (210) can also be arranged with a detector pitch (220), measured center to center between adjacent detector pixels (210), which determines minimum separation for different ions to be identified by the spatial detector (180). For example, if the system is designed to be able to separate an ion with mass of 400 amu from another ion with mass of 401 amu (e.g., assuming similar ion mobility), then the minimum separation required would be equal to the detector pitch (220) so that ions of 400 amu and 401 amu would be received by different detector pixels (210).

Each detector pixel (210) is capable of receiving ions and converting the received ions into a voltage signal. The voltage signal is by nature analog, but can be converted to digital (0 or 1) by, for example, passing the voltage signal through a comparator with a known threshold voltage. In one embodiment of the present disclosure, the spatial detector (180) can be a 1000 detector pixel (210) by 1000 detector pixel (210) array produced by complementary metal oxide semiconductor (CMOS) microfabrication technology.

FIG. 2B shows that the spatial detector (180) can have row and column decoders (250) so that each detector pixel (210) or each group of detector pixels has a distinct address that can be selected and read out by the readout module (190). For example, any number of detector pixels (210), from one detector pixel (210) to all of the detector pixels (210) in the spatial detector (180), can be selected to be read out in parallel by the readout module (190). FIG. 2B shows a read out method where four (4) pixels can be read out in parallel as a group (240).

As another example, if the system is configured to look for a target ion, such as Alanine ions, then the readout module (190) can select only the detector pixels (210) where Alanine is expected and read only these selected detector pixels (210). Such intelligent selection and readout performed by the readout module (190) can yield faster data acquisition.

By reading in parallel and/or only some detector pixels (210) rather than all of the detector pixels (210), the data acquisition and the identification of the ions by the system is generally faster. Additionally, this parallel and/or selective reading of the detector pixels (210) can allow for sampling in dynamic settings such as tracking changes in the environment and changes in the composition of the chemical compounds. Shorter acquisition times generally lead to lower power consumption, which is also a consideration in applications such as portable applications.

Addresses of the detector pixels (210) where a target ion is expected can be calculated based on the known ion mobility K of the target ion and the pulses of electric field applied to the chamber (160) through which the ions traverse during operation.

In another embodiment of the present disclosure, the addresses of the detector pixels (210) in the spatial detector (180) can be associated with known ions by calibration via measuring known ions in the system. By mapping each ion to the addresses of the detector pixels (210) that receive the ions and storing the mapping association in a lookup table, information on actual addresses at which the known ions arrive and voltage signals read from these actual addresses can be utilized by the chemical recognition module (195).

The chemical recognition module (195) can, for instance, adapt values in the lookup table based on the information obtained during the calibration. It should be noted that, in this embodiment, ion mobilities need not be known or measured explicitly since the detector pixels' (210) addresses are associated to and mapped by known ions.

It should also be noted that the chamber (160) and the spatial detector (180) can be designed such that the addresses of the detector pixels (210) correlated with each type of ion can display symmetry, which can be useful for separating actual data from noise data. For example, for chambers with circular cross sections and the entry portion (150) centered about the cross section, as shown in FIG. 1A, the detector pixels (210) correlated to one target ion can form a circle about the center of the detector, as shown in FIG. 3A.

Figure 3A:
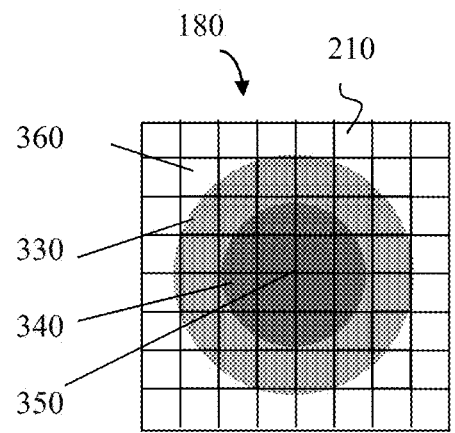
FIGS. 3A and 3B show an exemplary 2-D spatial detector receiving three target ions.

Specifically, FIG. 3A shows locations at which three target ions are received by the spatial detector (180). The ions received by each detector pixel (210) can be converted into a voltage signal. The voltage signals can also be converted to digital voltage signals by a comparator with a threshold voltage.

Figure 3B:
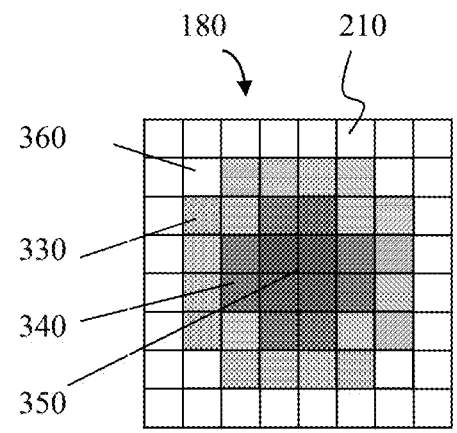

The resulting voltage signals are shown graphically in FIG. 3B, where the darkest shading shows the voltage signals for one target ion (350) while the lighter shading shows the voltage signals for another target ion (340), and the lightest shading shows the voltage signal for yet another target ion (330). The three target ions (330, 340, 350) are separated by the pulses of electric field applied to the chamber (160) of FIG. 1A or 1B.

In practice, there may be detector pixels (210) which may receive ions in only part of the detector pixel (210) since the detector pixels (210) are finite in size. One such pixel (360) that only partially receives an ion is shown in FIGS. 3A and 3B. A comparator circuit with a threshold can be used to read out these pixels and can generate a digital voltage signal of 1 or 0 for the partially receiving pixel (360) based on the amount of the particular ion received by the detector pixel (210). As shown in FIG. 3B, if the voltage signal generated by the particular ion at the partially receiving pixel (360) is below the threshold, then the partially receiving pixel (360) is considered as not having detected the particular ion.

Figure 5:
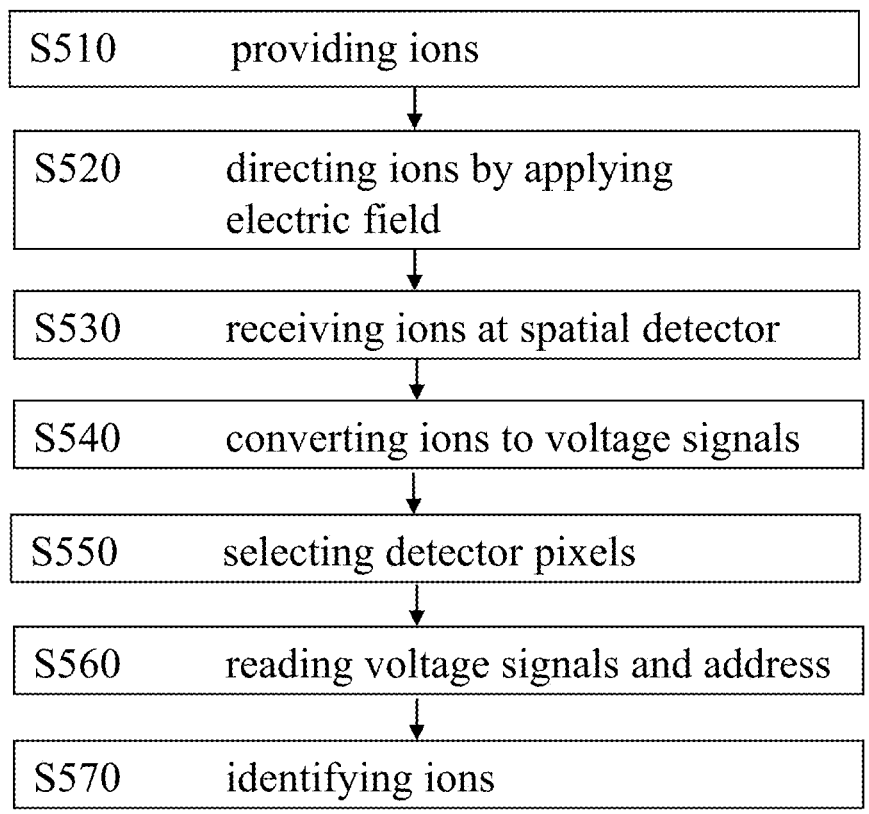
FIG. 5 shows a flow chart for an exemplary method for detecting and identifying ions.

FIG. 5 shows a flow chart for a method for detecting and identifying ions. The person skilled in the art will understand that the number of such steps shown in the method is only indicative and that the method can occur in more or fewer steps according to the various embodiments.

The method comprises providing ions (S510) to an entry portion (150) of a chamber (such as the chamber (160) of FIGS. 1A and 1B); directing the ions (S520) in the chamber (160) by applying a first set of pulses of electric field to the chamber (160); receiving a first set of ions (S530) at a spatial detector (such as the spatial detector (180) of FIGS. 1A and 1B), the spatial detector (180) comprising a first plurality of detector pixels (210) arranged in a two-dimensional array, wherein each detector pixel (210) is associated with an address and receives none, a subset or a full set of the ions in the first set of ions; converting the first set of ions (S540) to a set of first voltage signals; selecting detector pixels (S550) (210) from among the first plurality of detector pixels (210); reading the first voltage signal and the address (S560) of each selected detector pixel (210); and identifying ions (S570) received at each selected detector pixel (210) based on the first voltage signal and the address of each selected detector pixel (210).

Figure 4:
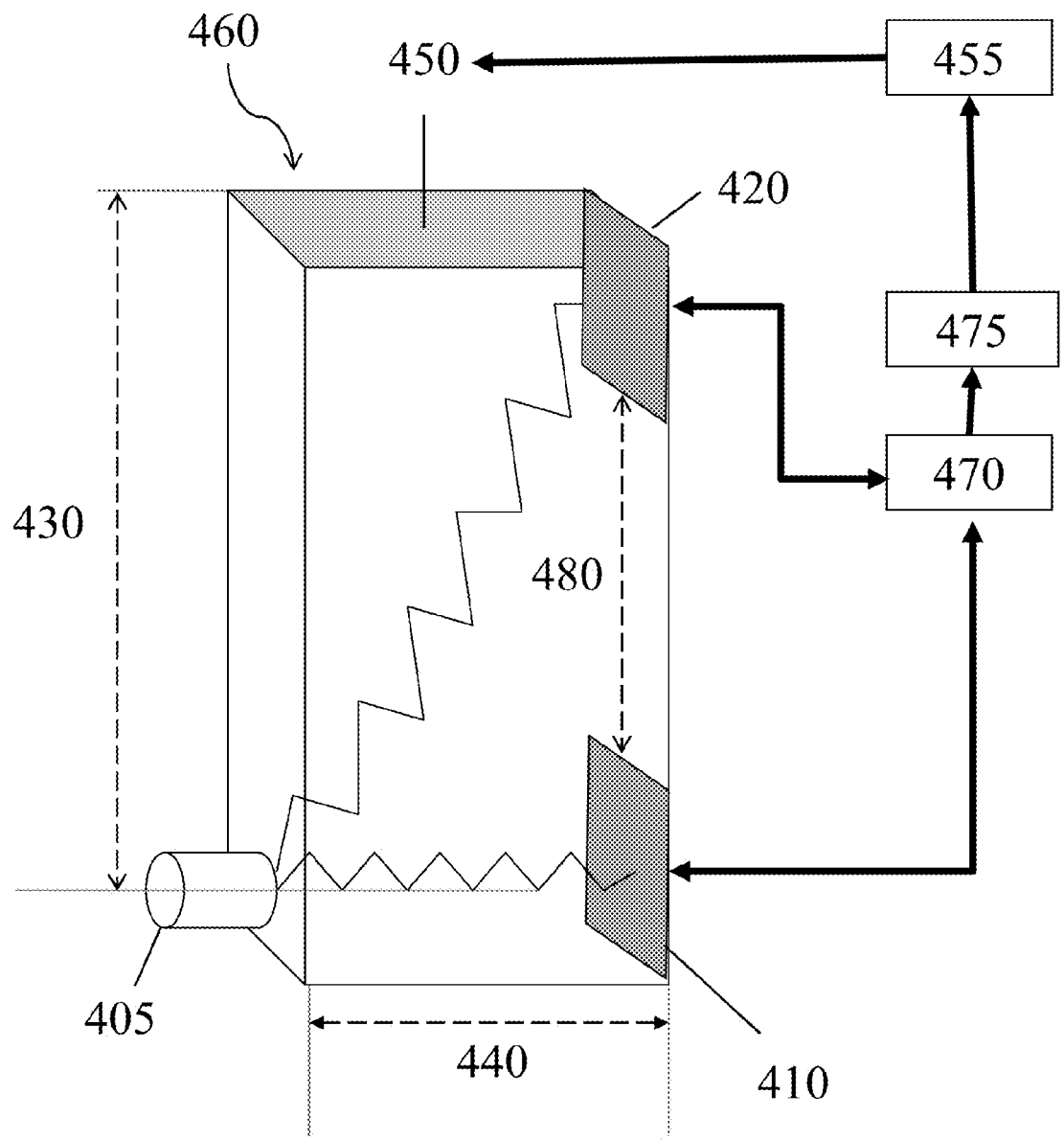
FIG. 4 shows an embodiment of an ion detection and identification system which comprises two detectors.

FIG. 4 shows an embodiment of the ion detection and identification system that comprises two detectors (410, 420). A first detector, referred to as a spatial detector (410), is used to detect a range of mass of ions at low resolution. A second detector, referred to as a separating detector (420), can be used to separate ions that are within a certain amu in mass, such as within 1 amu.

The system shown in FIG. 4 comprises a rectangular chamber (460) with two 2-D detectors: the spatial detector (410) and the separating detector (420), an ion entry portion (405), an electric field generator (450) coupled to the chamber (460), a readout module (470) coupled to both detectors (410, 420), a chemical recognition module (475) coupled to the readout module (470), and an electrical field controller (455) coupled to the chemical recognition module (475).

The chamber (460) of this embodiment is asymmetric with respect to the ion entry portion (405). In other words, the entry portion (405) is not centered about the cross-section of the chamber (460). Additionally, in the system of FIG. 4, the entry portion (405) is closer to the bottom plane of the chamber (460). This asymmetry will form a semicircular rather than circular shape on the spatial detector (410).

It should be noted that chamber height (430) and chamber length (440) determines ion separation capability, and thus ion identification capability, of the chamber (460) as defined by the equation $h=KEL/V_d$, previously provided in FIG. 6, where h is the height of the ion path (limited by the chamber height (430)), K is the ion mobility, E is the applied electric field, L is the chamber length (440) and $V_d$ is the drift velocity. In one embodiment of the present disclosure, the chamber length (440) is 2.0 cm and chamber height (430) is 6 cm to allow for a separation of 10 μm for ions with masses of 400 amu and 401 amu.

The embodiment with the spatial detector (410) and separating detector (420) allows for iterative and precise separation, which allow separation and accurate identification of ions with very close molecular masses and/or ion mobilities. For example, an ion sample can be directed to the separating detector (420) by the electric field generator (450). The detector pixels (210) of the separating detector (420) can convert the received ions into voltage signals which can be read by the readout module (470).

It is further noted that the separating detector (420) can be movable such that the separation distance (480) between the separating detector (420) and the spatial detector (410), as shown in FIG. 4, can be adjusted. This adjustability in location of the separating detector (420) yields a more flexible system configuration and can lead to more accurate and faster ion detection and identification.

Similar to other embodiments of this disclosure, the readout module (470) in the two-detector system shown in FIG. 4 can be an intelligent system that selects pixels for fast parallel reading or for selectively reading only those detector pixels (210) associated with a target ion. The readout module (470) can send the voltage signal and address information of the detector pixels (210) to the chemical recognition module (475), which can identify the ions or determine additional separation required for identification of the ions. As previously noted, the chemical recognition module (475) can be a lookup table that maps a particular ion, such as the target ion, to a particular detector pixel address or addresses. Additionally or alternatively, the chemical recognition module (475) can employ a more complex neural network unit for pattern recognition.

The chemical recognition module (475) can calculate the pulses of electric field required for further separation of the ions. The calculated requirement or data for the pulses of electric field can be received by the electric field controller (455), which adjusts the pulses of electric field applied by the electric field generator (450) to the chamber (460) according to the calculated requirement or data. The pulses of electric field separate the ions and direct the ions to the separating detector (420), where different ions are expected to be received at different detector pixels (210). FIG. 4 shows the electric field controller (455) as a separate unit from the chemical recognition module (475), but the electric field controller (455) can also be implemented as part of the chemical recognition module (475).

As previously mentioned, the ions received by the detector pixels (210) are converted to voltage signals, which are read by the readout module (470), and the voltage signals and addresses of the detector pixels (210) are received by the chemical recognition module (475), which identifies the ions. In practice, the calculated pulses of electric field do not always direct or separate the ions sufficiently so as to allow accurate detection and identification at the separating detector (420).

For instance, with reference to configuration of the system shown in FIG. 4, one or more of the ions of interest may be directed to a region between the two detectors (410, 420) or a top plane of the chamber (460). Consequently, the chemical recognition module (475) may iteratively calculate the pulses of electric field involved in accurate detection and identification and the electric field controller (455) may follow by iteratively adjusting the electric field generator (450) until the ions are detected and identified.

Additionally, at each iteration of the detection and identification process, the separation distance (480) between the spatial detector (410) and the separating detector (420) may be adjusted with or without adjusting the electric field generator (450).

Yet another mode of operation for this embodiment of the present disclosure may involve selecting a target ion. This mode of operation involves iteratively performing steps of reading only detector pixels (210) associated with the target ion and calculating and applying pulses of electric field until the target ion is detected and identified. This can be an efficient method when a desired result is simply a "yes" or "no" (e.g., 1 or 0) regarding presence of the target ion.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. For example, the person skilled in the art will understand that the number steps or components shown is only indicative and that the method can occur in more or fewer steps and that the system may contain more or less components according to the various embodiments. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A system for detecting and identifying ions, comprising:
an entry portion for ions;
a chamber through which the ions traverse during operation;
an electric field generator coupled to the chamber, wherein pulses of electric field generated by the electric field generator are adapted to direct the ions in the chamber;
a spatial detector configured to receive a first set of ions, the spatial detector comprising a first plurality of detector pixels arranged in a two-dimensional array, wherein a first group of detector pixels of the first plurality of detector pixels are associated with respective addresses and are configured to receive same first target ions of the first set of ions and to convert the first target ions into a first group of first voltage signals, wherein the first group of detector pixels are distributed in the two-dimensional array to define a geometric pattern;
a readout module adapted to select the first group of detector pixels from among the first plurality of detector pixels and read the first group of first voltage signals and the addresses of the selected detector pixels, thus detecting the same first target ions of the first set of ions; and
a chemical recognition module configured to receive the first group of first voltage signals and the addresses from the readout module and identify the same first target ions of the first set of ions based on the first group of first voltage signals and the addresses,
wherein the two-dimensional array is located at least at a longitudinal distance (L) in a longitudinal direction from the entry portion, wherein at least one dimension of the two dimensions of the two-dimensional array is based on a height direction for ions, the height direction being orthogonal to the longitudinal direction, and wherein a relationship between the longitudinal distance (L) and a height distance (h) in the height direction and an applied electric field (E) is given by $$h = \frac{K \times E \times L}{V_d}$$

where K is ion mobility and $V_d$ is drift velocity of ions.

2. The system of claim 1, wherein the spatial detector is located in the chamber.

3. The system of claim 1, wherein the spatial detector is located at an end or adjacent to the end of the chamber.

4. The system of claim 1, wherein the readout module is adapted to select and read a plurality of detector pixels in parallel.

5. The system of claim 1, wherein the readout module is adapted to select and read detector pixels associated with a target ion.

6. The system of claim 1, wherein the chemical recognition module comprises a neural network unit.

7. The system of claim 1, further comprising:
a separating detector configured to receive a second set of ions, the separating detector comprising a second plurality of detector pixels arranged in a two-dimensional array, wherein each detector pixel in the second plurality of detector pixels is associated with an address and is configured to receive at least one ion in the second set of ions, the second set of ions being a full set or subset of ions in the first set of ions, and is configured to convert the at least one ion into a second voltage signal; and
an electric field controller,
wherein:
the readout module is adapted to select detector pixels from among the first and second plurality of detector pixels and read the first and second voltage signals of the selected detector pixels,
the chemical recognition module is configured to:
receive the first and second voltage signals and the addresses from the readout module,
identify at least one ion in each of the first and second set of ions based on the first and second voltage signals and addresses of the selected detector pixels,
calculate data for a further set of pulses of electric field to direct the second set of ions to the separating detector, and
iteratively identify and calculate until at least one ion in the second set of ions is identified, and
the electric field controller is configured to receive the data for the second set of pulses of electric field from the chemical recognition module and to adjust the pulses of electric field applied to the chamber by the electric field generator based on the data.

8. The system of claim 7, wherein the separating detector is located in the chamber.

9. The system of claim 7, wherein the separating detector is located at an end or adjacent to the end of the chamber.

10. The system of claim 7, wherein location of the separating detector is adjustable.

11. The system of claim 7, wherein the readout module is adapted to select and read detector pixels in parallel.

12. The system of claim 7, wherein the chemical recognition module comprises a neural network unit.

13. The system of claim 1, wherein a second group of detector pixels of the first plurality of detector pixels are associated with respective addresses and are configured to receive same second target ions of the first set of ions and to convert the second target ions into a second group of first voltage signals, wherein the second group of detector pixels are distributed in the two-dimensional array to define a geometric pattern and wherein the second target ion is different from the first target ion.

14. The system of claim 13, wherein, in the two-dimensional array, the first group of detector pixels are differently located with respect to the second group of detector pixels.

15. The system of claim 1, wherein said first group of detector pixels are located symmetrically with respect to the chamber.

16. The system of claim 1, wherein the two-dimensional array and the entry portion are centered about a cross section of the chamber and said first group of detector pixels are located symmetrically about the center of the spatial detector.

17. The system of claim 1, wherein the first group of detector pixels are located symmetrically about a center of the spatial detector to define a circle.

* * * * *